(12) United States Patent
Just et al.

(10) Patent No.: US 10,206,617 B2
(45) Date of Patent: Feb. 19, 2019

(54) METHOD AND APPARATUS FOR NON-INVASIVE ANALYZING THE STRUCTURE AND CHEMICAL COMPOSITION OF BONE TISSUE ELIMINATING THE INFLUENCE OF SURROUNDING TISSUES

(75) Inventors: Marcin Pawel Just, Wroclaw (PL);
Przemyslaw Los, Zurawice (PL);
Michal Hugo Tyc, Wroclaw (PL)

(73) Assignee: Bone Vitae SA, Warsaw (PL)

( * ) Notice: Subject to any disclaimer, the term of this patent is extended or adjusted under 35 U.S.C. 154(b) by 93 days.

(21) Appl. No.: 13/579,939

(22) PCT Filed: Feb. 11, 2011

(86) PCT No.: PCT/PL2011/000014
§ 371 (c)(1),
(2), (4) Date: Oct. 12, 2012

(87) PCT Pub. No.: WO2011/102743
PCT Pub. Date: Aug. 25, 2011

(65) Prior Publication Data
US 2013/0204109 A1    Aug. 8, 2013

(30) Foreign Application Priority Data
Feb. 19, 2010 (PL) .................................. 390500

(51) Int. Cl.
*A61B 5/00* (2006.01)
*A61B 5/053* (2006.01)

(52) U.S. Cl.
CPC .......... *A61B 5/4504* (2013.01); *A61B 5/0537* (2013.01); *A61B 5/417* (2013.01); *A61B 5/4509* (2013.01)

(58) Field of Classification Search
CPC ..... A61B 5/4504; A61B 5/4509; A61B 5/053; A61B 5/0537; A61B 5/417
(Continued)

(56) References Cited

U.S. PATENT DOCUMENTS 3,885,552 A * 5/1975 Kennedy ......................... 607/27
5,203,344 A * 4/1993 Scheltinga ........... A61B 5/0535
600/547

(Continued)

FOREIGN PATENT DOCUMENTS

GB          2449226 B       11/2008
WO    WO 2008/119992 A2    10/2008
WO    WO/2011/102743 A1     8/2011

OTHER PUBLICATIONS

International Search Report PCT/PL2011/000014; and Written Opinion dated Jun. 29, 2011.

*Primary Examiner* — Rene Towa
*Assistant Examiner* — H. Q. Nguyen
(74) *Attorney, Agent, or Firm* — Nexsen Pruet, LLC; John B. Hardaway, III; Todd A. Serbin

(57) ABSTRACT

A method and apparatus for non-invasive analysing the structure and chemical composition of bone tissue eliminating the influence of surrounding tissues, is provided. The method consists in using a system of at least four electrodes (1, 2, 3, 4, 5, 6, 7, 8) placed in electrical contact with tissues surrounding the analysed bone, preferably a long bone to establish screening potential distribution using screening electrodes (7, 8). Measuring current injecting electrodes (1, 2) are used to force the measuring current flow through the internal part of the analysed bone. At the same time the screening electrodes (7, 8) reduce the measuring current flow through the tissues surrounding the analysed bone almost to zero. Then measuring current and potential at the measuring current injecting electrodes (1, 2) as well as phase (Continued)

difference between potential at measuring current injecting electrodes (1, 2) and measuring current are measured. On the basis of measured electrical values the structure and chemical composition of bones is evaluated.

9 Claims, 4 Drawing Sheets

(58) Field of Classification Search
USPC .......................................................... 600/547
See application file for complete search history.

(56) References Cited

U.S. PATENT DOCUMENTS

| | | | |
|---|---|---|---|
| 6,336,045 B1* | 1/2002 | Brooks | A61B 5/053 |
| | | | 600/407 |
| 6,631,292 B1* | 10/2003 | Liedtke | 600/547 |
| 6,760,616 B2* | 7/2004 | Hoey et al. | 600/547 |
| 2002/0072686 A1* | 6/2002 | Hoey et al. | 600/547 |
| 2002/0156378 A1 | 10/2002 | Sakal | |
| 2003/0176808 A1 | 9/2003 | Masuo et al. | |
| 2011/0082382 A1* | 4/2011 | Willers | A61B 5/0537 |
| | | | 600/547 |

* cited by examiner

METHOD AND APPARATUS FOR NON-INVASIVE ANALYZING THE STRUCTURE AND CHEMICAL COMPOSITION OF BONE TISSUE ELIMINATING THE INFLUENCE OF SURROUNDING TISSUES

FIELD OF THE INVENTION

The present invention relates to a method and apparatus for analysing the structure and chemical composition of bone tissue eliminating the influence of surrounding tissues, especially the structure and chemical composition of a spongy part of long bones using bio-impedance measurements.

BACKGROUND TO THE INVENTION

The known techniques for analysing the structure and chemical composition of bones consist in performing an X-ray or analysing ultrasound echo scan. The techniques using X-ray are distinguished by a very good specificity and sensitivity at 95% level in the case of a dual energy X-ray densitometry (absorptiomerty) method but they are time-consuming and troublesome/inconvenient. They involve exposing a patient to a harmful effect of X-ray and require using expensive sizeable equipment. The ultrasound methods are not very reliable as they are based on a measurement of mechanical properties of the bones which do not reflect the structure and chemical composition accurately.

A method for analysing bone structure described in the British Patent GB2449226 relates to bio-impedance spectroscopic measurements using an apparatus equipped with two measuring electrodes. The method consists in generating, with a use of a generator, at least one standard signal of a defined waveform which is applied to the bone tissue through the surrounding tissues, skin and muscles and then the electrical response which is a difference of potentials caused by current flowing through the analysed tissues is directed to the measuring system using the same electrodes. The data related to the bone tissue structure are generated in the system.

The apparatus consists of two electrodes connected to a generator of changeable, arbitrarily selected frequency standard ac current signal and a system monitoring electrical response of a measuring circuit with a computer generating output data. Both electrodes are used simultaneously for supplying the current and monitoring the response concerning the bone tissue density. This method allows to perform a quick, non-invasive and harmless bio-impedance measurement. However, it does not provide the possibility of distinguishing from bio-impedance signal the information describing electrical parameters of bone tissue alone, especially its spongy part which was intended to be the subject of analysis by the inventors of the quoted solution. This method does not distinguish that the vast majority of measuring current flows through the tissues surrounding the bones, i.e., muscles, fat tissue and skin which, in this case, are insignificant from diagnostic point of view. In addition, this method does not compensate for screening effect of the outer bone surface which is characterized by high impedance, which might decrease considerably the measuring current flowing through the inner bone structures.

SUMMARY OF THE INVENTION

A method in accordance with the present invention comprises a system of at least four electrodes placed on the skin covering the soft tissues surrounding the analysed bones, preferably a long bone, screening potential field is established by the screening electrodes and the flow of measuring current is forced through the analysed bone by the measuring current injecting electrodes. At the same time the screening electrodes reduce the flow of the measuring current passing through the soft tissues surrounding the analysed bone almost to zero. The measuring current and potential responses as well as a phase difference between the potential response and measuring current are measured at the injecting electrodes. Next on the basis of measured electrical parameters the structure and chemical composition of bones are determined.

It is advantageous that using the injecting electrodes the measuring alternating current passing through the surrounding tissues is directed to the analysed bone and at the same time alternating screening potential inside tissues surrounding the analysed bone is established at the screening electrodes, then at measuring current injecting electrodes the potential produced by the flow of measuring current is measured and the difference of measured potentials is evaluated while the value of the screening potential is maintained and regulated dynamically at the level proportional to the potential measured at the measuring current injecting electrodes.

It is also advantageous that during the measurement the frequency of injected measuring current changes at least once, and at the same time for each frequency of the injected measuring current the measuring current and the potential at the measuring current injecting electrodes are measured.

It is advantageous that the potential produced by the flow of the measuring current is measured with the additional electrodes measuring the potential produced by the measuring current flow while the probe electrodes are used to measure the real screening potential inside the tissues surrounding the analysed bone at the measurement points. In addition, at the screening electrodes the screening potential is established in such a way and for such measuring current is supplied to the injecting electrodes that the potential at each additional electrode is proportional to the potential at the probe electrode placed nearest to it, at the same time each of the additional electrodes is placed near different injecting electrode and each probe electrode is placed near different screening electrode. It has been found extremely advantageous when the potential at each additional electrode is equal to the potential at the probe electrode nearest to it.

The apparatus in accordance with the present invention comprises an interface for communication with a computer and a microprocessor control system with a keyboard and a display connected to a block of high sensitivity preamplifiers with a phase-sensitive detector and a system realizing dynamic screening in parallel and at least two electrodes are connected to the system realizing dynamic screening.

It is advantageous that the system realizing dynamic screening is connected to two electrodes measuring the potential produced by the measuring current flow, two probe electrodes and two screening electrodes.

It is advantageous that the probe electrodes and the screening electrodes which are placed between the probe electrodes are all positioned between the first pair of a subsystem of measuring electrodes which comprises a measuring current injecting electrode and an electrode measuring the potential of the measuring current flow and the second pair of a subsystem of measuring electrodes which comprises a measuring current injecting electrode and an electrode measuring the potential of the measuring current flow.

It has been found extremely advantageous that the first measuring current injecting electrode is placed on a clamp embracing the wrist of the subject adjacent the olecranon and the second measuring current injecting electrode is placed on the elbow support, the first electrode measuring the potential produced by the measuring current flow is positioned opposite to the electrode placed on the clamp embracing the wrist, the second electrode measuring the potential produced by the measuring current flow is positioned on the clamp embracing the arm adjacent the elbow while the electrodes measuring the potential at probe points as well as the electrodes injecting the current establishing the screening potential are placed on the bands embracing the middle part of the forearm and the electrodes are in the shape of rings or partially open rings.

It is advantageous that the first measuring current injecting electrode is placed on a clamp embracing the wrist of the subject adjacent the olecranon and the second measuring current injecting electrode is placed at the elbow support while the screening electrodes are positioned on the bands embracing the middle part of the forearm and the electrodes are in the shape of rings or partially open rings.

It is advantageous that the electrodes are limb clamp electrodes and the second measuring current injecting electrode is an integral part of the apparatus casing.

As will be appreciated the method in accordance with the present invention allows to eliminate the influence of the tissues surrounding the analysed bone using a measuring system comprising two electrode sets, i.e., a set of measuring electrodes and a set of screening electrodes. The measuring current is injected to the analysed system comprising a bone tissue surrounded by tissues of a different type using a measuring electrode set placed on the skin which is used simultaneously to measure the potential difference caused by the injected current flow.

The additional screening electrode set, at least two electrodes, produces in the tissue the additional potential reducing current flow through the tissues surrounding the analysed bone tissue. The additional electrodes are controlled dynamically using an electronic feedback system which provides optimal measuring conditions, i.e., minimizing the parasitic current flow through the tissues insignificant from the diagnostic point of view. Dynamic screening forces the measuring current to flow through the spongy part of a bone which allows to determine its electrical parameters.

High impedance of surface bone layers which in two electrode method practically makes an accurate measurement of bioelectric parameters of the internal bone parts impossible, in the case of using dynamic screening effectively stops any adverse influence of the screening current on the measurement results. In addition the method for determining bone tissue structure and chemical composition in accordance with the present invention allows to determine the structure and chemical composition especially a degree of spongy bone mineralization quickly and accurately which is significant in osteoporosis and osteopenia diagnostics. In comparison with other so far used methods the method in accordance with the present invention enables to eliminate the influence of other tissues surrounding the bone tissue on the measurement results.

As will also be appreciated the invention provides the possibility of producing a portable apparatus comprising an electrode system which can be placed on the body of a subject as well as a small size battery powered measuring device that can be connected to the PC by a wire or wireless connection providing galvanic insulation.

BRIEF DESCRIPTION OF THE DRAWINGS

An example of a method and an apparatus for performing the invention are now described with reference to the accompanying drawings, in which:

FIG. 3 shows the density of the analysed bone,

FIG. 4 shows the direction of the measuring current and the current produced by the screening potential, FIG. 5 shows the density of the measuring current and the current produced by the screening potential.

DESCRIPTION OF EXAMPLES

Example 1

Figure 1:
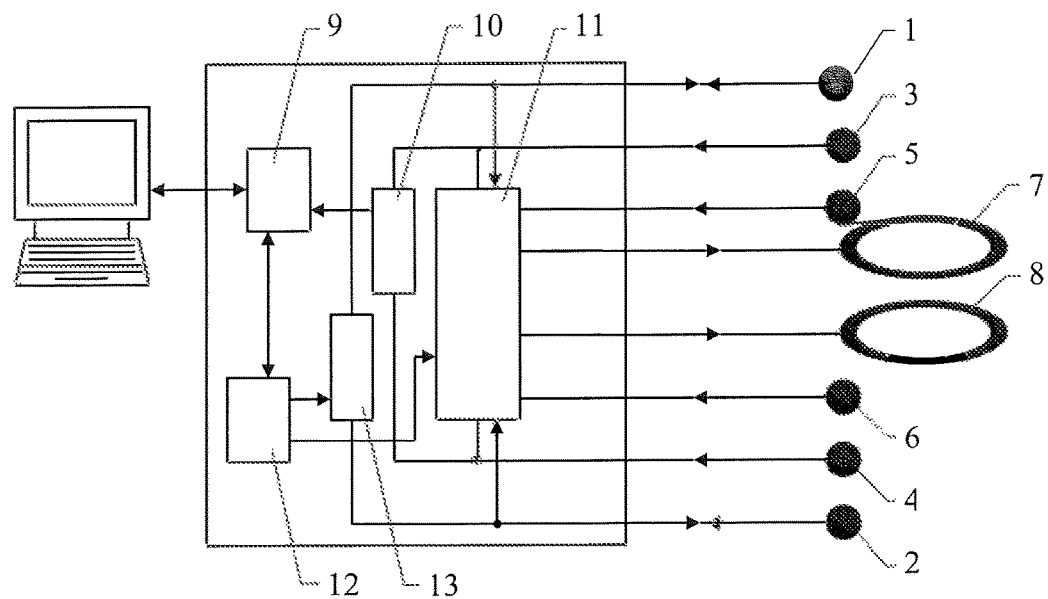
FIG. 1 shows a general schematic representation of apparatus for determining the structure and chemical composition of the analysed bone.
Figure 2:
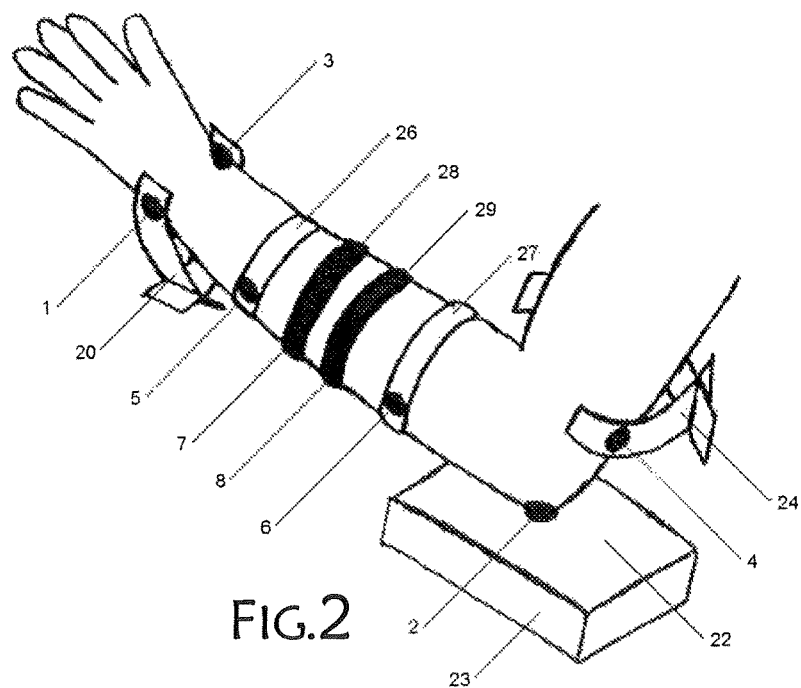
FIG. 2 shows the electrode distribution on the forearm.
Figure 3:
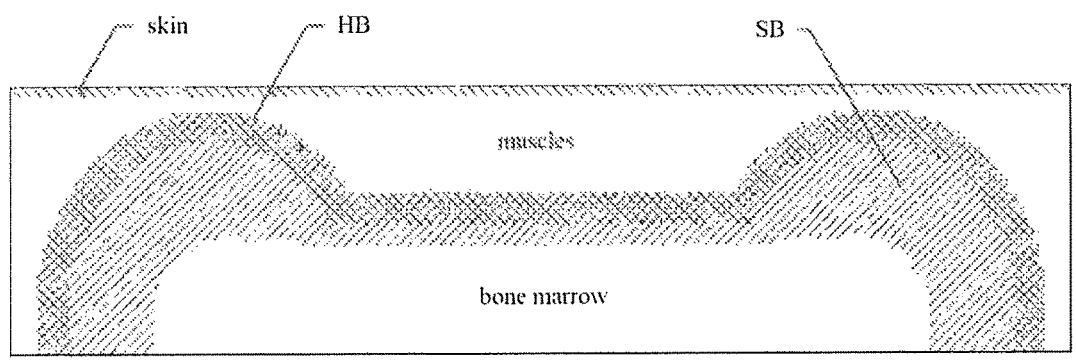
FIGS. 3, 4, 5 show a schematic cross section of the bone analysed using eight electrodes.

Method for non-invasive analysing the structure and chemical composition of bone tissue eliminating the influence of surrounding tissues consists in generating alternating measuring current $I_p$, which is supplied to the tissues surrounding the analysed bone by measuring current injecting electrodes 1, 2; at the same time alternating screening potential is established at the screening electrodes 7, 8 which forces the measuring current flow $I_p$ through the analysed bone. Screening potential value is regulated dynamically and maintained at a level proportional to the potential measured at the measuring current injecting electrodes 1, 2. The injected measuring current frequency changes at least nine times in equal intervals in the range from 250 Hz to 250 kHz during a measurement. Potential at the measuring current injecting electrodes 1, 2, measuring current $I_p$ value as well as a phase difference between the measuring current injecting electrodes 1, 2 and measuring current $I_p$ are measured for each of ten injected measuring current frequencies. On the basis of measured electrical values the structure and chemical composition of bone tissue are eveluated.

Example 2

A method for non-invasive analysing the structure and chemical composition of bone tissue eliminating the influence of surrounding tissues is carried out as in the Example 1 with the difference that the potential produced by the measuring current $I_p$ flow is measured with the electrodes measuring potential produced by the measuring current flow 3, 4 while the potential at probe points is measured with probe electrodes 5, 6. The injected electrical signal frequency is changed seven times. Potential at the electrodes measuring the potential produced by the measuring current flow 3, 4, measuring current $I_p$ value as well as the phase difference between the potential at the electrodes measuring the potential produced by the measuring current flow 3, 4 and measuring current $I_p$ are measured for each of eight injected measuring current $I_p$ frequencies. On the basis of measured electrical values the structure and chemical composition of bone tissues are evaluated.

Example 3

An apparatus for non-invasive analysing the structure and chemical composition of bone tissue comprises a microprocessor control system equipped with a keyboard and a display 12 connected to an interface that communicates with a computer 9. The microprocessor controlling system with a keyboard and a display 12 is connected to measuring current generating block 13 connected to two measuring current injecting electrodes 1, 2. A block of high sensitivity preamplifiers with a phase-sensitive detector 10 and a system realizing dynamic screening 11 comprising fast preamplifiers as well as fast output amplifiers are connected in parallel to the interface that communicates with a computer 9 and the microprocessor control system with a keyboard and a display 12. Two screening electrodes 7, 8 are connected to the system realizing dynamic screening 11.

Example 4

An apparatus for non-invasive analysing the structure and chemical composition of bone tissue is the same as in the Example 3 with the difference that two additional electrodes measuring the potential produced by the measuring current flow 3, 4 as well as two probe electrodes 5, 6 are connected to the system realizing dynamic screening 11. Probe electrodes 5, 6 and screening electrodes 7, 8 making up the screening electrodes subsystem are placed between the first pair of measuring electrode subsystem comprising a measuring current injecting electrode 1 and an electrode measuring the potential produced by the measuring current flow 3 and the second pair of measuring electrode subsystem comprising a measuring current injecting electrode 2 and an electrode measuring the potential produced by the measuring current flow 4. In the screening electrodes subsystem, screening electrodes 7, 8 are placed between probe electrodes 7, 8.

Example 5

An apparatus for non-invasive analysing the structure and chemical composition of bone tissue is the same as in the Example 4, with the difference that a measuring current injecting electrode 1 is placed on a clamp 20 embracing the wrist adjacent olecranon, a measuring current injecting electrode 2 is placed on an elbow support 22, an electrode measuring the potential produced by the measuring current flow 3 is positioned opposite the electrode 1 on the clamp 20 embracing the wrist, an electrode measuring the potential of the measuring current flow 4 is placed on the clamp 24 embracing the arm adjacent the elbow while probe electrodes 5, 6 as well as screening electrodes 7, 8 are positioned on the bands 26, 27, 28, 29 embracing the middle part of a forearm. The electrodes 7, 8 are in the shape of partially open rings.

Example 6

An apparatus for non-invasive analysing the structure and chemical composition of bone tissue is the same as in the Example 3 with the difference that the measuring current injecting electrode 1 is placed on the clamp 20 embracing the wrist adjacent olecranon and the second measuring current injecting electrode 2 is positioned at an elbow support 22 which is an integral part of the apparatus casing 23. Screening electrodes 7 and 8 are in the shape of partially open rings and electrodes 1, 7, 8 are limb clamp electrodes.

The system operates in such a way that measuring current $I_p$ and the potential at measuring current injecting electrodes 1, 2 as well as the phase difference between the potential at the measuring current injecting electrodes 1, 2 and the measuring current $I_p$ are measured in contact with tissues surrounding the analysed bone tissue using the electrodes 1, 2, 7, 8 composed of two subsystems which function as measuring and screening electrodes. Using a pair of measuring current injecting electrodes 1 and 2, the measuring current $I_p$ is injected and using a pair of the electrodes measuring the potential produced by the measuring current flow 3 and 4, the potential difference produced by the measuring current $I_p$ flow through the tissues surrounding the analysed bone tissue is measured. The potentials at the established probe points are measured using a pair of probe electrodes 5 and 6, and the current establishing the screening potential is injected using a pair of screening electrodes 7 and 8. The positions of the screening electrodes 7 and 8 are established so as to have them placed between the groups of the electrodes measuring the potential produced by the measuring current flow 3 and 4 of opposite potential. A system realizing dynamic screening 11 containing fast amplifiers is used to obtain the assumed path of the measuring current $I_p$ flow in the tissue.

For the purpose of the analysis a bone is selected, in which hard bone HB surrounds spongy bone SB filled with bone marrow, preferably a long bone, on the skin covering the muscles, on which all electrodes could be placed including the mutual configuration of probe electrodes 5, 6 and screening electrodes 7, 8 between the groups of measuring current injecting electrodes 1, 2 and the electrodes measuring the potential of the measuring current flow 3, 4 of opposite potential.

In addition, the bone is selected in such a way that insulating action of hard bone HB layer allows to use without any negative influence, the screening electrodes 7, 8 to analyse spongy bone SB tissue. Preferably the best region of the human body to be analysed is a forearm at which probe electrodes 5, 6 and screening electrodes 7, 8 in the shape of clamping ring in the middle part of a forearm are placed while measuring current injecting electrodes 1, 2 and electrodes measuring the potential of the measuring current flow 3, 4 are placed on the skin adjacent olecranon near the wrist and the elbow, respectively.

Figure 4:
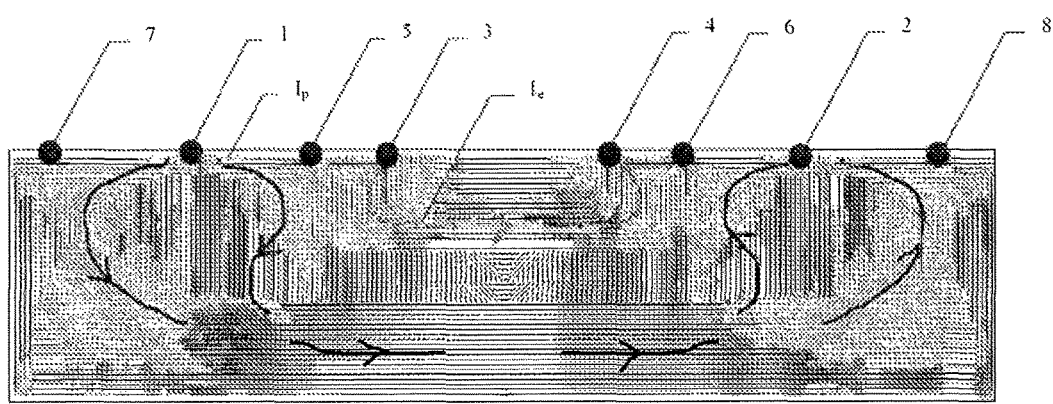
Figure 5:
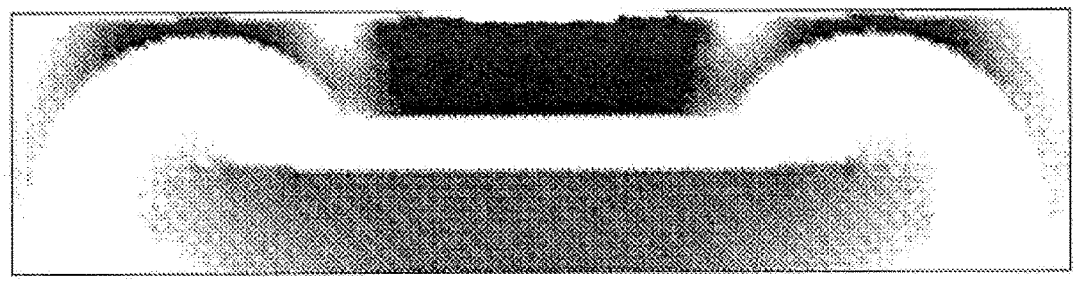

The arrows and the line direction in FIG. 4 which correspond to the analysed directions of the measuring current $I_p$ flow as well as the current $I_e$ produced by the screening potential flowing through the analysed tissues and current density $I_p$, $I_e$ (FIG. 5) show distinctly that the screening potential forces the measuring current $I_p$ to flow through the analysed bone tissue omitting the tissue surrounding it; while current $I_e$ of the screening potential thanks to the insulating properties of the external layer does not permeate its inside. Shades of grey in FIG. 5 mark current density values; the lighter shades correspond to high values while the darker ones correspond to low values.

Sensitivity of an apparatus according to the present invention defined as a relative measured change of electrical values observed when electrical parameters of the analysed bone tissue are changed by 10% is presented in Table.

| Frequency of measuring current [Hz] | Sensitivity of known two electrode device | Sensitivity of an apparatus according to the invention |
|---|---|---|
| 100 | 0.016% | 4.8% |
| 1000 | 0.16% | 4.7% |
| 10000 | 0.55% | 4.8% |
| 100000 | 0.58% | 6.4% |

As it has been presented in the Table the apparatus analysing the structure and chemical composition of bone tissue eliminating the influence of surrounding tissues in accordance with the present invention is characterised by a very high sensitivity surpassing even hundred times the known device sensitivity.

The invention claimed is:

1. A non-invasive method for analysing characteristics of bone tissue within a human subject, comprising the steps of:
   attaching two electrode pairs including, a pair of measuring current injecting electrodes and a pair of screening electrodes, to soft tissue surrounding a bone to be analysed;
   imparting a measuring alternating current ($I_p$) through the soft tissue surrounding said bone to be analysed and through said bone through the measuring current injecting electrodes;
   measuring the potential produced by the measuring current ($I_p$) imparted through the soft tissue and the bone;
   simultaneously applying an electrical screening potential through the screening electrodes at a level proportional to the measured potential produced by the measuring current ($I_p$), to reduce the measuring current ($I_p$) through the soft tissue to substantially zero;
   measuring any remaining measuring current ($I_p$) and the potential of the analysed bone at the measuring current injecting electrodes to determine characteristics of the analysed bone based upon measured electrical values.

2. The method according to claim 1 further comprising: repeating said step of imparting at different alternating current frequencies.

3. The method according to claim 1 further comprising:
   Attaching a pair of measuring electrodes and a pair of probes to said soft tissue surrounding said bone, and wherein said step of measuring the potential produced by the measuring current ($I_p$) is carried out through said measuring electrodes.

4. The method according to claim 1 wherein the measuring current injecting electrodes and the measuring current ($I_p$) is supplied indirectly through the soft tissue surrounding the bone to be analysed at the same time the screening potential inside the soft tissue surrounding the analysed bone is established at the screening electrodes, then the potential through the bone produced by the measuring current ($I_p$) is measured at the measuring current injecting electrodes and the phase difference between the measured potential through the bone and the measuring current ($I_p$) is evaluated while the value of the screening potential is maintained at the level proportional to the potential measured at the measuring current injecting electrodes.

5. The method according to claim 3, wherein the potential in the analysed bone produced by the measuring current ($I_p$) is measured by the measuring electrodes while the screening potential in the soft tissue surrounding the analysed bone is measured by the probes.

6. The method according to claim 3 wherein the potential in the soft tissue and analysed bone at each of said measuring electrode is proportional to the measured potential in the soft tissue and analysed bone at one of said probes closest to one of said measuring electrodes, and wherein each of said measuring electrodes is placed near a different measuring current injecting electrode and each probe is placed close to a different screening electrode.

7. The method according to claim 6 where the screening potential and the measuring current are applied so that the screening potential at each of said measuring electrode is equal to the measured potential in the soft tissue and analysed bone at the nearest probe.

8. The method according to claim 3 wherein the probes and said screening electrodes are placed between said measuring current injecting electrodes.

9. The method according to claim 8 wherein a first electrode of said measuring current injecting electrode pair is placed on a first clamp embracing said subject's wrist adjacent an olecranon thereof and a second electrode of said measuring current injecting electrode pair is placed on an elbow support,
   a first electrode of said measuring electrode pair is positioned on said first clamp opposite the first measuring current injecting electrode and a second electrode of said measuring electrode pair is placed on a second clamp embracing the arm of the subject adjacent the elbow, wherein the probes and the screening electrode pair are placed on bands embracing a middle part of the subject's forearm and wherein said screening electrode pair are each in the shape of rings.

* * * * *